United States Patent [19]

Manzie, Jr.

[11] 4,389,878
[45] Jun. 28, 1983

[54] DYNAMIC GAS TRANSMISSION MEASURING APPARATUS

[75] Inventor: Otter L. Manzie, Jr., Saginaw, Mich.
[73] Assignee: The Dow Chemical Company, Midland, Mich.
[21] Appl. No.: 259,768
[22] Filed: May 1, 1981
[51] Int. Cl.³ .......................................... G01N 15/08
[52] U.S. Cl. ..................................................... 73/38
[58] Field of Search ........................................... 73/38
[56] References Cited
U.S. PATENT DOCUMENTS 3,256,732 6/1966 Gremion .................................. 73/38
3,590,634 7/1971 Pasternak .............................. 73/38

FOREIGN PATENT DOCUMENTS

184499 2/1966 U.S.S.R. ................................. 73/38

Primary Examiner—S. Clement Swisher
Attorney, Agent, or Firm—R. B. Ingraham

[57] ABSTRACT

Gas transmission rates for and taken across plastic specimens are accurately measured in suitable apparatus for the purpose by a dynamic technique involving constant measurement of pertinent temperature and pressure data which is permitted to constantly change throughout the measurement testing.

4 Claims, 10 Drawing Figures

$N_2 + He_2$ Runs at 200°F

○ - GT Cell #1
□ - GT Cell #2

DYNAMIC GAS TRANSMISSION MEASURING APPARATUS

BACKGROUND OF THE INVENTION

There are several known gas transmission measuring devices available and in fairly extensive employment on and in the market. Prominent and widespread in application amongst these are The Dow Gas Transmission Cell (ASTM Designation D-1434-66T) available from Custom Scientific Instruments, Inc. of Whippany, N.J. 07981 and the Linde Permeability Cell (ASTM Designation D1434), also available from the same mentioned commercial source.

The available gear for the indicated purpose, including those above specifically identified, generally require a constant pressure drop and temperature in order to obtain the desired permeation data. These requirements, as is well comprehended by those skilled in the art, impose some disadvantageous limitations and disabilities on the known apparatus and uses thereof.

Thus, for indicated testing purposes, nothing in prior art appears to realistically concern itself with a truly dynamic way of measuring the transmission rate of various gases through curved or flat plastic sheets, liners, films, etc. in the same efficient and extremely reliable manner, well-adapted for commercial testings and investigations, in the style and means of implementation as is so crucially indigenous as is present and involved in the instant contribution to the art.

FIELD AND PURVIEW OF THE INVENTION

The present invention, and the principle aims and objectives attainable in its practice, pertain(s) and direct(s) to a novel and, in the overall, unprecedented and exceptionally efficient and technically accurate means and technique for measuring the gas transmission rate(s) of various plastics materials (including, for example but without limitation thereto, samples of tubular sections, sheets, film, laminates, plastic-coated paper and metal specimens, etc.) when subjected to permeation by various inert and/or corrosive gases and/or vapors.

The achievement and provision of all indicated, with even more and additionally other benefits and advantages derivable in and from present practice appear and become more evident in the ensuing description and Specification.

SUMMARY OF THE INVENTION

The present invention, in its genesis and as derives from the discovery on which it is based, pertains to the indicated novel technique (as well as to the associated means combination in apparatus assembly for the implementation thereof) for dynamically determining the rate of transmission of a given gas (including vapors) by and through a sample of a given plastic material whose gas permeation characteristic is desired to be defined and measured which, in basic outline, comprises: taking a sample of given surface area subject to facially-transgressing permeation thereacross by the given gas of a given plastic material (of which said plastic constitutes at least a coated or laminate part if not the entirety of the sample) whose gas permeation rate characteristic is being (or wanted to be) determined; mounting said sample in a confined and retained manner in such a way that it can be exposed within its controlling confines to gas under a given (or pre-selected) maximum test pressure to be applied against the upstream side of the sample face to be thereby exposed with a reduced or (at least at test commencement, zero) gas pressure effective on and behind the opposing downstream side face of the sample; then, at constant given temperature, constantly applying for a given time period the gas involved in the test at said maximum pressure against the exposed upstream face of said sample; permitting the gas during said time period to permeate and transgress said sample; measuring continuously or from time-to-time within said test time period the dynamically changing pressure drop from upstream to downstream side faces of and across said sample; noting and collecting the critical involved time(s), temperature(s) and pressure(s) data; and, finally, calculating from the collected data according to appropriate mathematical and physical laws and principles relevant thereto the particularly-involved gas transmission rate of and for said plastic material.

Apparatus embodimentation, as noted, of the contemplated technique is also here envisaged and intended as an integral part of the invention.

Still other features and adaptations of beneficial import and salience are advantageously combinable in and made integral part(s) of the basic and above fundamentally-delineated efficient technique and means for dynamic gas transmission rate determination of plastics materials pursuant to the invention.

Thus, various suitable procedures, modes of operation, precautions, instructions, parts, elements, subassemblies and overall assemblies plus other equipage and practices for utilization, as well as working details, embodimental parameters and other specifics of the invention are also set forth in the following Specification.

ILLUSTRATED EXEMPLIFICATION OF THE INVENTION

The invention is pictorially demonstrated in and by the ten (10) views of the accompanying Drawing (a number of which, for simplicity and convenience, are illustrated in a somewhat schematic and/or fanciful manner of representation and one of which is a graphical, data-depicting protrayal and all of which, insofar as possible, utilize the same reference numerals and letter designations for like and/or similar parts and/or elements and/or implementations) wherein, as they are to be taken in conjunction with the Specification that follows:

FIG. 9, analogous to but more expanded than the showing of FIG. 8, is a flow-sheet representation sort of view of an advantageous form of test unit installation in which three (3) test samples are simultaneously measured for gas transmission rate characteristics in three (3) separate but simultaneously operated cell housing units.

For expedience and enhanced clarity of: associated parts, elements and functions; subassemblies and assemblies; certain companion accessories, procedures and so forth; and results; reference is now thereto had to all such predominant componential features and manner and consequence(s) of their operations as they appear throughout the accompanying Figures included in the Drawing with explanation thereof in the following catalogued description of same as they are identified by their respective reference numeral(s) or letter designation(s) (i.e., "Ref. No(s).") therewith joined.

Figures 1, 2, 3, 4:
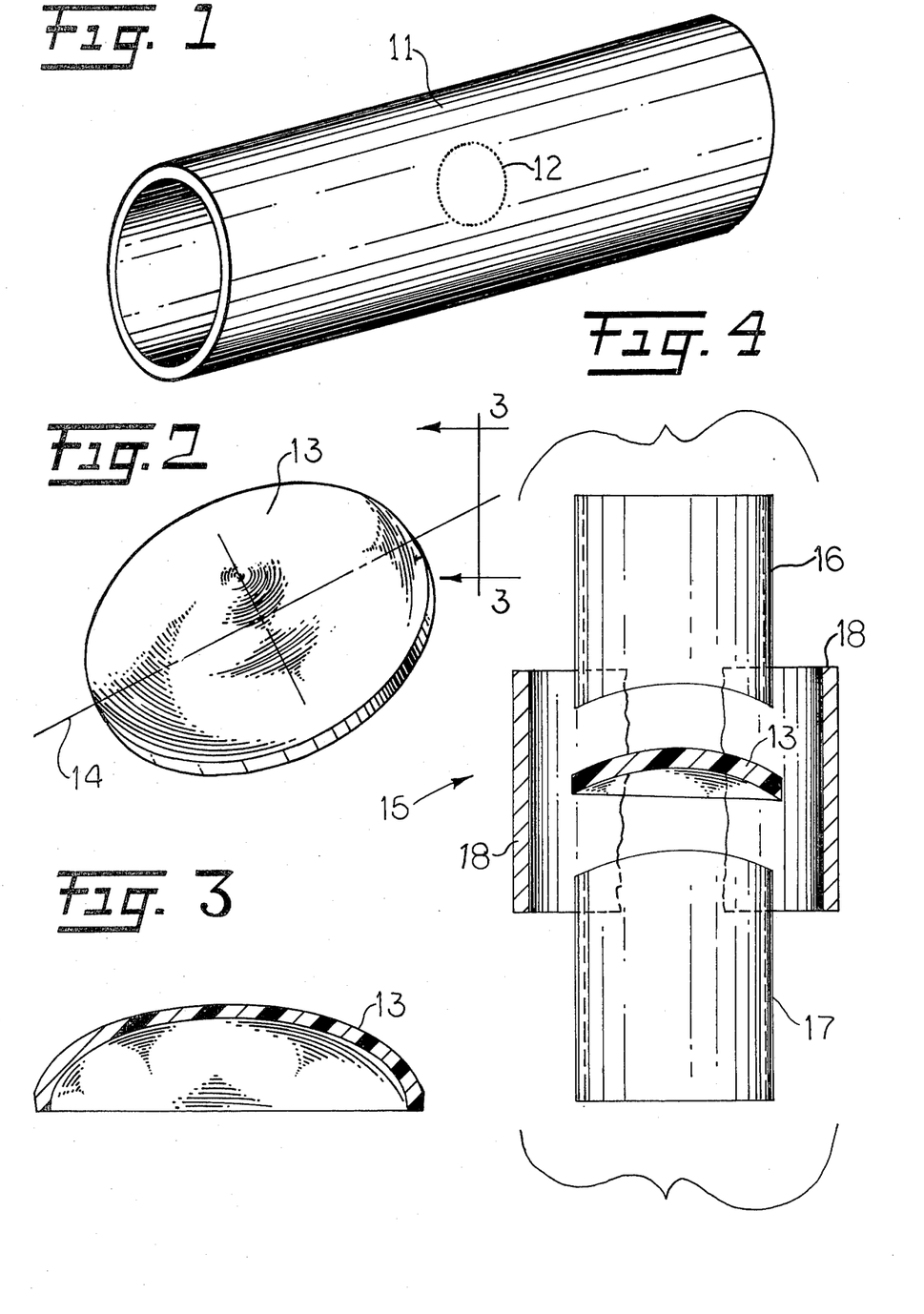
FIG. 1 is a perspective view of a tubular form fabricated from a plastic material (such as a polypropylene liner section intended for the outfitting of plastic-lined metal pipe product) from which a sample for gas transmission rate testing and determination can be taken.
FIG. 2 is a perspective view of a circular, dished-form sample for testing taken from the tubular specimen illustrated in FIG. 1.
FIG. 3 is a side elevation view, taken along the line 3—3 in FIG. 2, of the plastic material sample illustrated in FIG. 2.
FIG. 4 is a fanciful side elevation view, partly broken away and partly in section, of a typical cell housing unit in which to mount and test the plastic material sample specimen to determine the gas transmission rate thereof.
Figures 5, 6, 7:
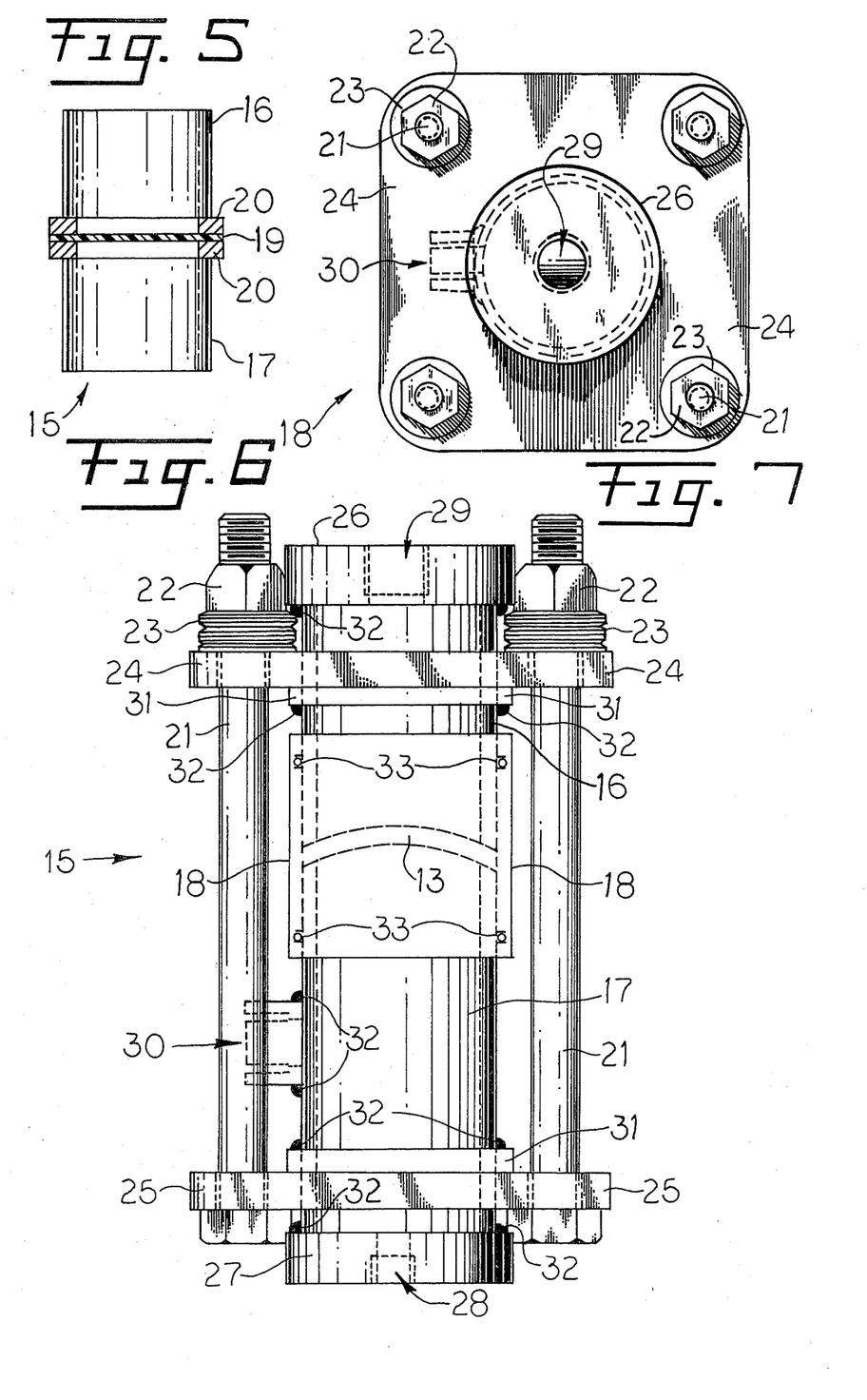
FIG. 5 is another fanciful side elevation view illustrating a cell adapted to contain for testing a flat plastic material sample specimen.
FIG. 6 is a side elevation view of one embodiment of sample-containing and -mounting cell for utilization in practice of the invention, showing greater structural detail and practical embodimental construction than is illustrated in the relatively schematic cell representations of FIGS. 4 and 5.
FIG. 7 is a top or plan view of the cell unit detailed in FIG. 6.
Figure 6:
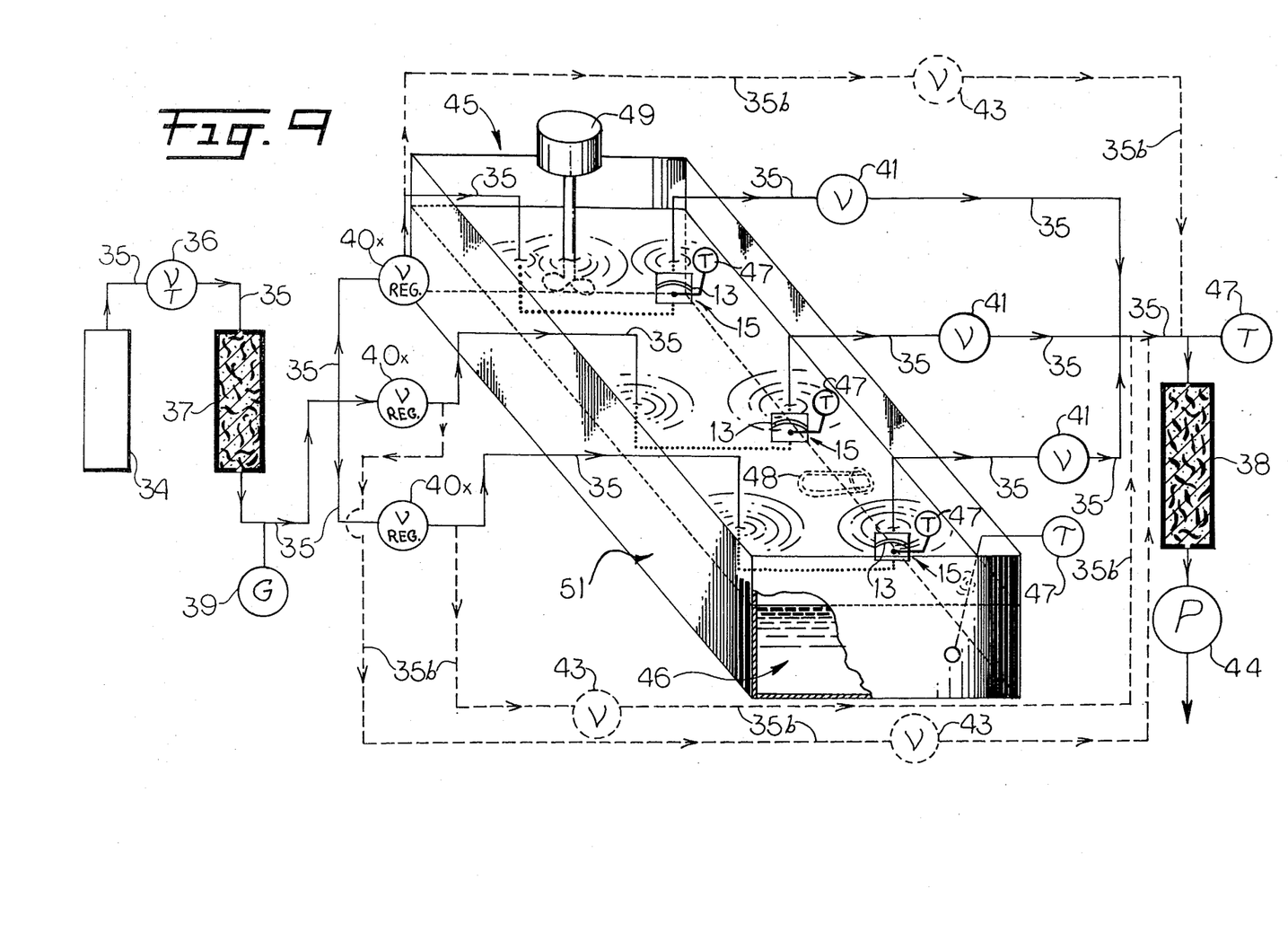

| Ref. No(s). | Description With Relevant Corollary Explanation |
|---|---|
| 11 | Length of plastic material tubing or pipe, such as a liner for plastic lined pipe, from which a specimen is to be taken for determination of the gas transmission rate of the involved plastic. |
| 12 | Phantom line representation of hole saw cut to be taken to obtain specimen for testing. |
| 13 | Cut out specimen or dish-like form (as is obtained from supply stock of tubular material). |
| 14 | Center line of specimen 13. |
| 15 | General designation of cell housing unit for mounting of specimen to be tested. |
| 16 | Upper housing section of cell cut out along lower peripheral edge to conform to curved specimen to be mounted in the cell. |
| 17 | Lower housing section of cell cut out along upper peripheral edge to conform to curved specimen to be mounted in the cell. |
| 18 | Sealing sleeve (shown broken apart and in partial section in FIG. 4) to envelope upper and lower housing sections 16 and 17 about the area of specimen mounting which usually is a more or less vertically central location in the cell. |
| 19 | Flat specimen for testing (shown only in FIG. 5), as may be taken from sheet or film stock or coated paper or laminated metal specimens; it being advantageous for any sample to be tested to have a diameter between about 2–3 inches (ca. 5.08–7.62 centimeters) while taken for the measurement purpose in a generally circular form, whether its contour be curved or flat. |
| 20 | Sealing washers (shown only in FIG. 5) for assisting the firm and leak proof mounting of a flat or otherwise conformed sample to be tested. |
| 21 | A bolt with a hexagonal head to secure the upper and lower halves together of the form of cell embodiment illustrated in FIGS. 6 and 7 of the Drawing. |
| 22 | The nut(s) for bolt(s) 21. |

| Ref. No(s). | Description With Relevant Corollary Explanation |
|---|---|
| 23 | The spring washer(s), or equivalent, to utilize with bolt(s) 21 and nut(s) 22 for clamping together of the cell unit shown in FIGS. 6 and 7. |
| 24 | The top or upper clamping plate for assembly of the FIGS. 6 and 7 cell unit. |
| 25 | The bottom or lower clamping plate for the FIGS. 6 and 7 cell unit. |
| 26 & 27 | Upper and lower cover caps, respectively, for cell unit of FIGS. 6 and 7. |
| 28 | Gas or vapor inlet port, identified by general designation. |
| 29 | General designation of gas or vapor outlet port. |
| 30 | General designation for thermal well to facilitate gas temperature measurement in the cell unit portrayed in FIGS. 6 and 7. |
| 31 | Welded-on retainers or collars to engage with upper and lower clamping plates 24 and 25 to secure assembly of cell housing. |
| 32 | Weld spots or lines. |
| 33 | "O"-ring gaskets to facilitate sealing of circumenveloping sleeve unit 18. |
| 34 | Gas (or vapor) supply (FIG. 8) |
| 35 | Pipe or tubing lines or conduits for gas interconnections, etc., in assembly arrangement. |
| 36 | Throttle valve. |
| 37 | Inlet filter, advantageously of the molecular sieve variety. |
| 38 | Outlet filter, also advantageously a molecular sieve. |
| 39 | Pressure gauge or recorder. |
| 40 | Regulating valve in gas conduits 35 on upstream side of cell. |
| 41 | Stop (control) valve in main gas handling line on downstream side of cell 15. |
| 35b | By-pass conduits. |
| 43 | Stop (control) valve in by-pass evacuation line. |
| 40x | Individual inlet control regulating valves in lines 35 upstream of cells 15. |
| 45 | Receptacle or reservoir container for heat exchange liquid medium, such as a flat pan, drum or the like or equivalent for an oil (or other heat-exchanging liquid) medium. |
| 46 | General designation of the heat exchanging fluid contained in the reservoir container 45. |
| 47 | Thermocouple unit or other equivalent and suitable temperature measuring means. |
| 48 | Immersion heater for temperature elevation and regulation of heat-exchanging fluid medium 46. |
| 50 | General designation of overall single cell test unit plan (FIG. 8 only). |
| 51 | General designation of overall triple cell test unit layout (FIG. 9 only). |

With an overview of the several depictions, views and illustrations of the Drawing being maintained (especially in the light of the foregoing explanations of parts, components, etc., and other elucidations), the subsequent portion of this Specification now turns to a somewhat more cohesive and particularized disclosure and exposure of and coordinated amplification upon the invention; including therein most appropriate and expedient (or best) manners and means stemming from the foregoing in which the same may be advantageously and propitiously embodied and practiced.

In this connection, the basic principles and limitations of: gas transmission rates and the mathematics and physics, such as ideal gas laws, therewith associated; the taking of plastic materials samples of testing; the handling and usage of both inert and possibly reactive gases and vapors; valving, pumps; temperature controls; vacuum systems; gas-drying assemblies; data taking, recording and application; suitable materials of construction for handling various materials of the type here involvable; and so forth are so widely comprehended by those skilled in the art that greatly elaborated detailing and/or fundamentals-explanation of all the basics thereof is not herein made or attempted; the same being unnecessary for thorough understanding and recognition of the advance possibilitated for achievement and realization by and with the development in and of the outstanding dynamic gas transmission rate procedure and realization improvement that is according to and in keeping with the present invention.

PARTICULARIZED OPERATION AND USE DESCRIPTION OF THE INVENTION

As is clearly evident in and readily-enough deducible from the foregoing description and disclosure, the present invention in basic essence and substance contemplates the provision for use and application of a dynamic system for determination of gas transmission rate(s) through plastic materials in which the pressure drop across the sample of plastic being tested and the rate of transmission through the plastic sample is continuously changing throughout the test run for the desired measurement. The present technique, most advantageously, offers what in effect is a self-monitoring system with the maximum temperature(s) and pressure(s) capable of utilization limited only by the withstanding ability against such factors of the plastic material, per se, being tested.

Some of the characteristics and particulars of the instant contribution to the art that, perhaps, are not completely-abundantly-plain in and from the foregoing Specification are now more precisely expostulated, including some optimum features prescribable for practice of the invention.

The basic and outstanding advantage and hitherto unknown benefit of the present invention is its capability, not available in other known systems, to dynamically measure the gas transmission rate without dependence on gathering data only at given pressure differentials across the sample undergoing test. By virtue of the instant development, only the temperature need be held constant while permitting the pressure differential to constantly change as the gas or vapor involved in the testing is permeating the sample.

The accessories and means utilized in embodimentation of the invention, such as valves, conduits, pumps, heaters, filters, etc., are of the generally standard and widely-utilized and -available types and styles commonly employed and as individual preference may dictate or select for laboratory and test equipment usage. It is usually desirable for the materials of construction employed to be of an inherently corrosion-resisting nature, such as stainless steel, Monel metal and so forth. The actual cell housing is often beneficially fabricated from such a material as "HASTALLOY" (Reg. TM). In this connection, an ordinarily convenient size for a cell unit built along the lines demonstrated in FIGS. 6 and 7 of the Drawing is something on the order of about 4 inches (ca. 10.16 centimeters) in width and about 12 inches (ca. 30.48 centimeters) in height, both overall. While the sample mounting section of the cell and general shape of the sample to be tested is usually preferably cylindrical and circular, respectively, other sample-holding cell chamber cross-sectional configurations and corresponding sample shapes may be utilized, including square, rectangular, other polygonal such as triangular and otagonal, etc. As is readily apparent, when flammable gases or vapors are involved, it is desirable to utilize explosion-proof motors, connectors and other items of equipment utilized.

In performance of the testing in keeping with preferable practice of the present invention, it is generally most beneficial and conductive of best results to allow any given run to proceed for a time period sufficient to allow the overall system, insofar as concerns upstream applied pressure relative to downstream accumulated pressure about the testing cell, to reach an equilibrium point or (and oftentimes even better) until the downstream accumulated gas or vapor pressure achieved by permeation across the sample under test equals the upstream pressure applied on the face of the sample undergoing measurement. Depending on particular temperature and pressure conditions utilized, the appropriate time period for this may be as long as 4-6 days and sometimes even longer.

Figure 8:
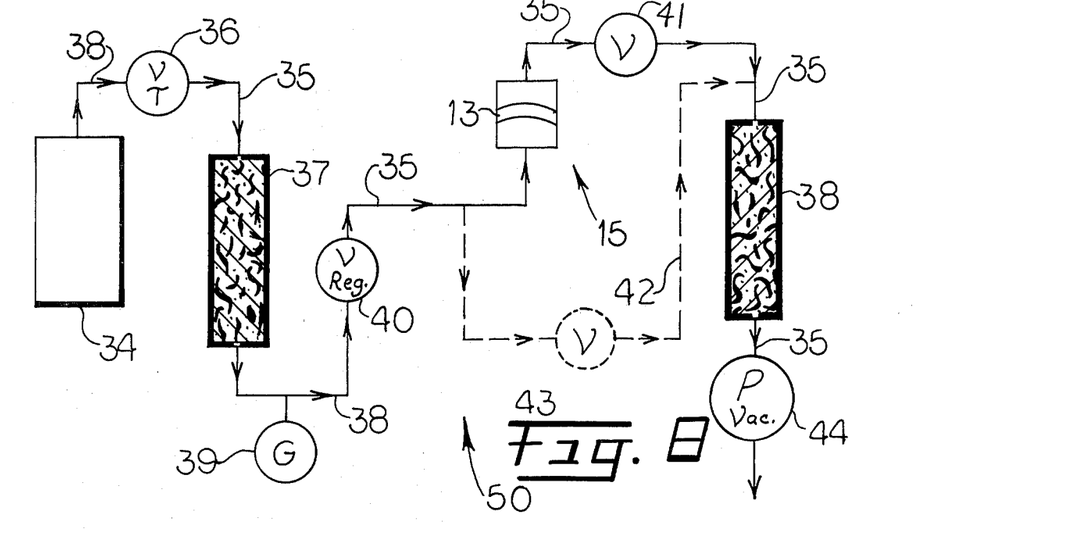
FIG. 8, in a more-or-less flow sheet style of schematic representation, is a view of a fundamental test installation including basic accessory components therefor for practice of the present invention.

A good reference for test operation with a typical system implementation in accordance with the present invention involves the following operational steps:

(a) Set high temperature cut-out controls to desired maximum temperature limits;

(b) Set the oil (or other heat-exchanging media) bath temperature heater (48 in FIG. 9) such as to effect the desired control temperature for the cell unit(s) 15 within the oil bath 46 in reservoir container 45;

(c) Turn on the agitator when one is employed (as 49 in FIG. 9);

(d) Switch on the bath heater (as 48 in FIG. 9);

(e) Set the desired pressure of gas or vapor to be applied over the upstream face of the sample 13 by regulation of throttle (or equivalent) valve 36;

(f) Open the main gas valve(s) feeding to the system for pressure regulation thereinto (as 40 in FIG. 8 and 40x in FIG. 9);

(g) Open the inlet pressure valve 36;

(h) Check the inlet or upstream gas or vapor being applied and regulate same to get desired reading (frequently, depending on precise installation involved and plastic material sample being tested on the order of about 150 pounds per square inch absolute (i.e., "psia");

(i) Start up the vacuum pump 44;

(j) Open the gas inlet valves 40 and/or 40x to the cell unit(s) 15;

(k) Open the cell by-pass valve 43 in by-pass line 35b for ≦30 or seconds—then close same;

(l) Hold the oil or other bath temperature at the desired set point for 24 or so hours;

(m) Close the downstream gas outlet valve(s) 41;

(n) Turn off pump 44, meanwhile (o) Noting and/or recording all pertinent time, temperature and pressure data;

(p) Wait until the system reaches equilibrium or until collection volume cell pressures reach a predetermined suitable maximum (such as, say, about 50 psia), continuing appropriate data gathering, then (q) With the obtained data, calculate the desired gas transmission rate value of the involved sample.

To obtain the gas transmission rate figure or value characteristic of the involved plastic material sample tested, it is advantageous to use formulae derivable from the clasic Ideal Gas Law using for the purpose the information contained in the Appendix to ASTM Method D-1434-66 (1972) entitled "Gas Transmission Rate of Plastic Film and Sheeting" as a model to follow.

Thus, the following equations that apply are developed:

$$n = \frac{P_t V_t}{RT} \quad (1)$$

wherein:
n = the number of moles of gas (or vapor) involved at given time "t";
P = the applied pressure in mm of Hg;
V = the involved volume in cm$^3$;
R = a universal gas constant; and
T = the involved temperature in °K.
t = value at time t.
From Equation (1), there is associated the expression $$RTn = P_t V_t, \quad (2)$$

in which the actual moles of gas transmitted is the change of "n" with "t" (time) per the expressive denotation:

$$dn/dt, \quad (2')$$

so that:

$$RT \frac{dn}{dt} = P_t \frac{dv}{dt} + V_t \frac{dP}{dt} \quad (3)$$

Since the downstream (or "collecting") volume is constant in systems embodied in accordance with the present invention, it logically follows that:

$$-dv/dt = 0 \quad (4)$$

providing for the mathematical statement that $$RT \frac{dn}{dt} = V \frac{dP}{dt} \quad (4')$$

Accordingly, since $$\frac{dn}{dt} = \frac{V}{RT} \cdot \frac{dP}{dt}, \quad (5)$$

then and thereby letting $$\frac{dP}{dt} = \frac{P_2 - P_1}{t_2 - t_1}, \quad (5')$$

wherein:
$P_2$ = the pressure at time $t_2$; and
$P_1$ = the pressure at time $t_1$.
It logically follows from the foregoing, utilizing the appropriate calculus thereto and therefor, that:

$$\frac{dn}{dt} = \frac{V}{RT} \left( \frac{P_2 - P_1}{t_2 - t_1} \right). \quad (6)$$

Since the GTR is a function of the "driving pressure" (i.e., "$P_d$", which in actuality is the difference in pressure on each side of the transmitting membrane or like or equivalent) and the involved transmitting area (i.e., "A"), it can be concluded that:

$$GTR = \frac{V}{RT} \left( \frac{P_2 - P_1}{t_2 - t_1} \right) \times \frac{1}{P_d A}, \quad (7)$$

wherein:
$P_d = P_i - P_t$, in which
$P_i$ = the inlet (or upstream) pressure; and
$P_t$ = the pressure at any given time "t".
With respect to the above given Equation (7), it can be taken into account that when the thickness of a given sample undergoing test (taken in mils, i.e., 0.001 inch or 0.00254 centimeter per mil) is utilized in place of unity over the "$P_d A$" term, the resulting value obtained is the "permeation coefficient" for the involved material.

In any event and in further regard of Equation (7), it can be set forth that for time periods in which the pressure of the transmitted gas (or vapor) is increasing linearly with time, the value according to following Equation (8) can be obtained when $P_t$ is averaged over the time period $t_1$ to $t_2$, namely:

$$P_t = \frac{P_1 + P_2}{2}, \quad (8)$$

and $$P_d(\text{average}) = P_i - \frac{P_1 + P_2}{2} = \frac{2P_i - P_1 - P_2}{2}. \quad (8')$$

Substituting Equation (8') above into Equation (7), it is thereby mathematically provided that:

$$GTR = \frac{V}{RT} \left( \frac{P_2 - P_1}{t_2 - t_1} \right) \left( \frac{2}{2P_i - P_1 - P_2} \right) \left( \frac{1}{A} \right). \quad (9)$$

One common system of units for reporting GTR's, at least in the United States of America, is in cm$^3$/24 hr. atm. per 100 in$^2$.

From Equations (5) and (7), it can be stated that:

$$GTR = \frac{dn}{dt} \times \frac{1}{P_d A}. \quad (10)$$

Pursuing that to arrive at figures or values in the above indicated units for GTR:

$$GTR = \frac{\frac{dn}{dt} \frac{\text{moles}}{\text{min.}} \times \frac{24 \times 60 \text{ min.}}{24 \text{ hrs.}} \times 22{,}415 \frac{\text{cm}^3}{\text{mole}} \times \frac{760 \text{ mm. Hg}}{\text{atm.}} \times 100 \text{ in.}^2}{P_d \text{ mm. Hg} \times A \text{ in.}^2}, \quad (11)$$

$$GTR = \frac{V}{ART} \left( \frac{P_2 - P_1}{t_2 - t_1} \right) \left( \frac{2}{2P_i - P_1 - P_2} \right) (1440 \times 22{,}415 \times 760 \times 100). \quad (11')$$

Thus:

$$GTR = \frac{4.9062 \times 10^{12} \, V(P_2 - P_1)}{ART(t_2 - t_1)(2P_i - P_1 - P_2)}, \quad (12)$$

for which:

$R$ is a universal gas constant having the value $62,360 \, \frac{cm^3 \, mm. \, Hg}{T \, gm. \, mole}$; and $T$ = Temperature in °K. or $5/9$ (°F. $-32$) + 273.16
$= 5/9$ (°F. $-17.78 + 273.16$)
$= 5/9$ °F. $+255.38 = 5°$ F. $+ 2298.42 \div 9$.

Substituting for R and T in Equation (12):

$$GTR = \frac{9 \times 4.9062 \times 10^{12} \, V(P_2 - P_1)}{62,360(5° \text{F.} + 2298.42) \, A(t_2 - t_1)(2P_i - P_1 - P_2)}. \quad (13)$$

Accordingly and in conclusion for calculation purposes:

$$GTR = \frac{7.0808 \times 10^8 \times V \times (P_2 - P_1)}{(5° \text{F.} + 2298.42) \, A(t_2 - t_1)(2P_i - P_1 - P_2)}, \quad (14)$$

wherein °F=the test temperature taken in °F.

In line with indications previously herein made, and as is intrinsically evident in the foregoing equational formula for GRT calculation, one great advantage in adaptation of the present invention to previously known techniques is that, even though the involved pressure differential is changing all of the time throughout the time period involved in the test (i.e., the "$\Delta P - P_d$" factor, as is the rate of moles of gas or vapor permeated through the sample a result of the "dn/dt" factor so as to cause constantly differing conditions in performance of the test), the same accurate GRT value will always be found.

To particularly illustrate tests run in practice of the present invention, three (3) individual samples having a generally dished and curvilinear contour with a thickness of about ¼ inch (ca. 0.635 centimeter) were cut into about 2½ inch (ca. 6.35 centimeters) diameter from a nominal 3-inch (ca. 7.62 centimeters) diameter section of tubular extrudate of "TEFLON" (Reg. TM) Brand polytetrafluoroethylene material obtained from E. I. duPont deNemours & Co., Inc. of Wilmington, Del. 19899. Usually an assembly analogous to that depicted in FIG. 9 of the Drawing, the samples (after precise average thickness determination of each) were loaded into the three (3) accommodating cells utilized and, after assembly therein, were placed in the constant temperature oil bath. The above-described start up procedure first using nitrogen gas; after which the gas transmission rate was determined per the foregoing Equation (14). Following this, another run was made on identical samples with more nitrogen gas; and then yet another run with helium gas.

Figure 10:
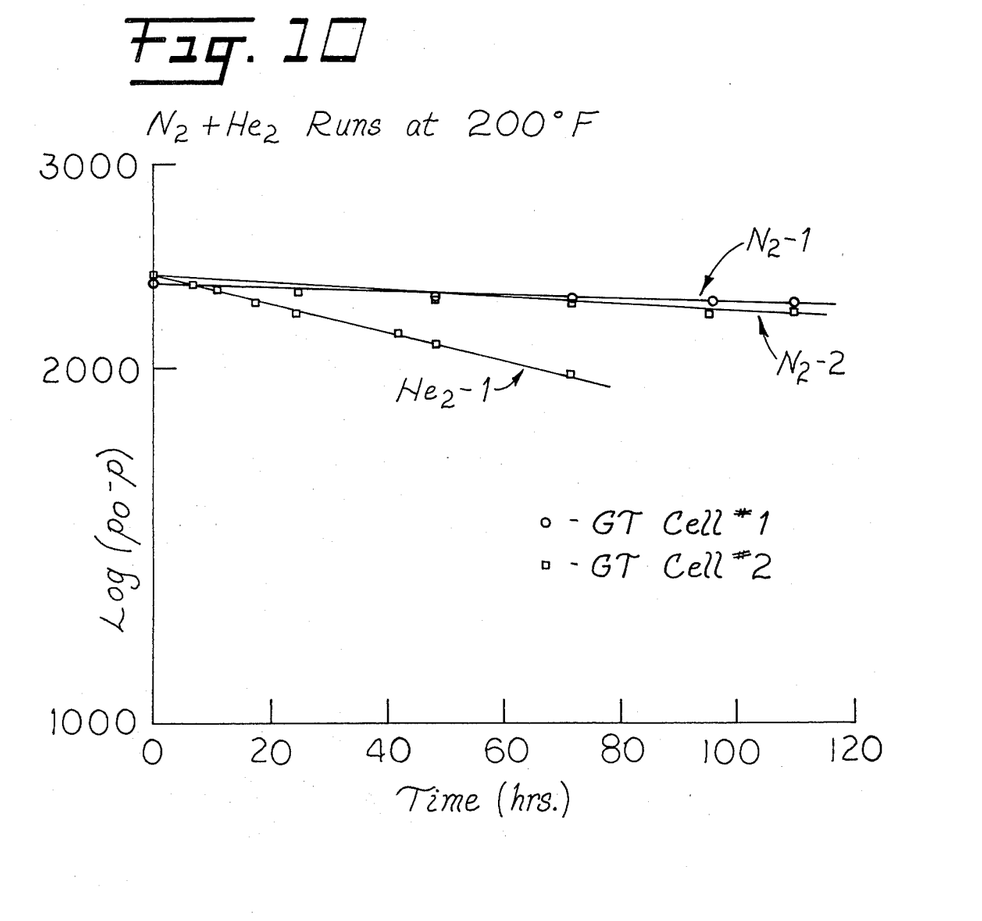
FIG. 10 is a graphical protrayal of test results obtained in measurements made in accordance with the present invention.

The results obtained are set forth in the graphical representation of FIG. 10 of the accompanying Drawing. In connection with that, it is to be noted that if the log of the difference between the inlet (or upstream) and outlet (or downstream) pressures of the gas utilized in each test are plotted versus time, the slope of the resulting linear curve is proportional to the associated gas transmission rate.

In correlation with the indicated results, the following tabulation sets forth the determined permeation coefficients (available in the indicated Equations) for each sample and gas tested with literature values given for same.

TABLE
Obtained Permeation Coefficients Gotten In Testing vs. Literature Values*

| Gas Involved | Line N-1 In FIG. 10 Graph | Line N-2 In FIG. 10 Graph | Literature Value Given As L-1 |
|---|---|---|---|
| Nitrogen | 1,900 | 2,400 | 1,500 |
|  | Line H-1 In FIG. 10 Graph | Literature Value Given As L-2 | Literature Value Given As L-3 |
| Helium | 11,100 | 9,500 | 16,500 |

*Note:
In the given determinations, allowances for various manufacturing processes of involved materials and miniscule density differences were not taken into account; even though and notwithstanding, such differences are obviously and clearly of a very small order of magnitude.

By way of recapitulation, it is plain from the foregoing that, in comparison with the system and embodimentation thereof of the present invention (here, referred to, as a matter of convenience in identification, as a "DyGTC"), the predominant equivalent units of prior art apparatus and procedure for the same purpose are quite inferior. These are the above mentioned "Dow Gas Transmission Cell" (presently called, also for convenience, the "DGCT") and the "Linde Permeability Cell" (likewise presently called the "LPC").

Thus, as has been brought forth:

(i) The DGTC and the LPC require a constant $\Delta P$ and temperature in order to secure accurate data; whereas the present DyGTC requires only constant temperature (which may result in shorter actual test run consummation times to arrive at suitable GRT values);

(ii) The DGTC is temperature limited—usually operable at only about normal Room Temperatures, this being due to the differences in expansion coefficients involved for the three (3) diverse materials utlized in operation thereof;

(iii) The DGTC is pressure limited (this being usually at atmospheric pressure or less), whereas the DyGTC as well, candidly compared, as the LPC is (are) pressure and temperature limited according to the characteristics in such particulars of the particular plastic material in the sample being tested; and (iv) The LPC is not self-monitoring, whereas both the DyGTC and the DGTC are.

In connection with the immediate foregoing and regardless of its operational superiority, DyGTC units pursuant to the present invention are commonly found to be only approximately half to one-third as costly to embody or procure as are DGTC and/or LPC apparatus installations.

Many changes and modifications can be readily made in and adapted to embodiments and practices in accordance with the present invention without substantially departing from its apparent and intended spirit and scope, all in pursuance and accordance with same as it is set forth and delineated in the hereto-appended Claims.

What is claimed is:

1. Dynamic technique for determining the rate of transmission of a given gas (including vapor(s)) by and through a sample of a given plastic material whose gas permeation characteristic is being measured which comprises, as Steps of the technique:
   (I) taking a sample of given plan-view surface area subject to facially-transgressing permeation thereacross by the given gas of a given plastic material whose gas permeation rate characteristic is being determined;
   (II) mounting said sample in a confined and retained manner in such a way that it can be exposed within controlling confines to gas under a given maximum test pressure to be applied against the upstream side of the sample to be thereby and thereto exposed with a reduced or zero gas pressure effective on the opposing, downstream side face; then,
   (III) at constant given temperature, constantly applying for a given time period involved and utilized in the test the gas at said maximum pressure against the exposed upstream face of said sample;
   (IV) permitting the gas during said test time period to permeate and transgress said sample;
   (V) measuring continuously or from time-to-time within said test time period the dynamically changing pressure drop from upstream to downstream side faces of and across said sample undergoing test;
   (VI) Noting and collecting the critical involved time(s), temperature(s) and pressure(s) data gatherable from the system, and finally
   (VII) calculating from the collected data the particularly-involved gas transmission rate of and for said plastic material, including the step of taking a generally circular, relatively dish-shaped and curvilinear sample from plastic tubing for the sample involved in said Steps (I) and (II).

2. Operating the technique of claim 1 at a maximum temperature and/or maximum pressure up to either of the limits for same of the plastic material undergoing testing therein.

3. Operating the technique of claim 1 for a period of time required for the downstream gas pressure after the sample is at equilibrium with the upstream gas pressure applied to the sample.

4. Operating the technique of claim 1 for a period of time required for the downstream gas pressure after the sample is at least approximately equal to the upstream gas pressure applied to the sample.

* * * * *